(12) United States Patent
Rose

(10) Patent No.: US 6,476,911 B1
(45) Date of Patent: Nov. 5, 2002

(54) BACKSCATTER INSTRUMENT FOR MONITORING PARTICULATE LEVELS IN A GAS STREAM

(76) Inventor: Thomas H. Rose, 2116 Oakton Dr., Raleigh, NC (US) 27606

( * ) Notice: Subject to any disclaimer, the term of this patent is extended or adjusted under 35 U.S.C. 154(b) by 0 days.

(21) Appl. No.: 09/701,845
(22) PCT Filed: Jun. 11, 1999
(86) PCT No.: PCT/US99/13019
§ 371 (c)(1), (2), (4) Date: Feb. 20, 2001
(87) PCT Pub. No.: WO99/64841
PCT Pub. Date: Dec. 16, 1999

Related U.S. Application Data
(60) Provisional application No. 60/089,196, filed on Jun. 12, 1998.

(51) Int. Cl.$^7$ .............................................. G01N 21/00
(52) U.S. Cl. ...................................... 356/337; 356/342
(58) Field of Search ................................. 356/337, 338, 356/342, 335, 336; 250/574

(56) References Cited

U.S. PATENT DOCUMENTS

| | | | | |
|---|---|---|---|---|
| 4,017,186 A | * | 4/1977 | Shofner et al. ............. | 356/103 |
| 4,176,960 A | * | 12/1979 | Eckbreth et al. ............ | 356/338 |
| 4,435,093 A | * | 3/1984 | Krause et al. .............. | 374/129 |
| 4,871,251 A | * | 10/1989 | Preikschat et al. .......... | 356/336 |
| 5,451,787 A | | 9/1995 | Taylor ..................... | 250/338.5 |
| 5,751,423 A | * | 5/1998 | Traina et al. ............... | 356/338 |
| 5,815,264 A | * | 9/1998 | Reed et al. ................. | 356/336 |

* cited by examiner

Primary Examiner—Michael P. Stafira
(74) Attorney, Agent, or Firm—Richard S. Faust

(57) ABSTRACT

An automatic setup backscatter particulate monitor includes a small source (38) of narrow beam radiant energy directed into a gas stream containing particulates. A lens (34) that is mounted behind the radiant energy source (38) collects the energy reflected back from the particulates and concentrates it on a photodetector (48). The beam is directed into duct at an angle greater than twice the beam spread, minimizing reflection off opposing wall surfaces. Internal radiant energy sources are periodically directed to the detector to verify system integrity. Backscattered energy is corrected for energy reflected from the opposite stack wall and for ambient energy.

20 Claims, 4 Drawing Sheets

BACKSCATTER INSTRUMENT FOR MONITORING PARTICULATE LEVELS IN A GAS STREAM

The PCT application was published in English This appl is a Prov No. 60/089,196, filed Jun. 12, 1998.

FIELD OF THE INVENTION

The invention relates to monitoring the amount of finely divided material in a fluid sample. More particularly, the invention relates to monitoring the level of particulates in a gas stream, for example, the dust in a smokestack or duct associated with baghouse pollution control equipment. The invention detects backscattered radiant energy as the means for monitoring particulate levels.

DESCRIPTION OF THE PRIOR ART

Environmental considerations have given rise to regulations requiring the monitoring of particulates in smokestacks and ducts. Initial instrumentation efforts consisted of transmissometers. A transmissometer is a device that projects a beam of light through a particulate-laden gas stream to a photodetector. The transmission of the light is attenuated by the particulates. The degree of attenuation is reported in terms of percent opacity. A number of these devices were developed and installed on smokestacks in the United States and elsewhere. These devices are reliable for the measurement of the opacity of particulates in a gas stream when the opacity exceeds 5%. Below 5% opacity these instruments are not reliable indicators of gas stream particulates because of optical alignment problems and linearity validation problems. Industrial transmissometers are costly, heavy, bulky, and not suitable for the measurement of low dust levels in the small stacks and ducts from industrial air pollution control equipment, particularly the small stacks and ducts associated with baghouse-type pollution control equipment.

Scattering instruments have been developed that measure the presence of particulates by projecting radiant energy into the gas stream and measuring the radiant energy scattered by the particulate. These instruments do not have alignment problems and have a high signal to noise ratio, allowing very low particulate level measurement. These instruments may be side scatter, forward scatter, or backscatter.

Side scatter instruments project a beam of radiant energy into the stack and collect the radiant energy from a section of the beam with a lens that focuses the energy onto a detector. Side scatter instruments have reduced sensitivity to increasing particulate loading due to the opacity of the gas stream between the beam section and the receiving lens. Further, only a small portion of the stack or duct is sampled resulting in incorrect assumptions of particulates loading across the gas stream, unless the particulates are evenly distributed (which rarely occurs).

Forward scatter instruments use a laser beam to project into the gas stream and monitor the forward scattered light from the particulates. These instruments have an advantage in that they can determine the size of a particle from the angle of the energy scattered by the particle. The sample volume is very small reducing this technique's utility. Because of size, weight and cost considerations, forward scatter instruments are not suitable for monitoring of dust levels in the small stacks and ducts associated with industrial air pollution control equipment.

Back scatter instruments use a projected beam of radiant energy that reflects off particles and is returned to a detector. There is no attenuation of signal as the level of particulate increases as the optical path to any particle reflecting energy will be clear if the projected beam and reflected energy are in the same path. Backscatter instruments usually use a laser to project adequate energy into the duct to assure a return signal. Reflections off the opposing wall are a concern in the measurement process. Many of these instruments are bulky, costly, and heavy rendering them unsuitable for measuring particulate levels in the small stacks and ducts from industrial air pollution control equipment.

The current practice in monitoring dust in the stacks and ducts associated with baghouse-type pollution control equipment is the use of monitors having non-optical probes that extend into the stacks or ducts and generate a measurement of particulate levels by the static charges that incident particles impart to the probe. These devices have the disadvantage of being operative only for use where the particulates being measured hold a charge. Also, these devices have reduced sensitivity and accuracy when the surfaces of the probes become dirty. Probe-type devices as described above are manufactured by Triboflow, Inc. (USA).

There is a need for an optical monitoring system that may be used with relatively small diameter stacks and ducts (for example, less than about five feet diameter) and having particulates therein at opacity levels that are relatively low (for example, less than about five percent opacity) as is the condition in the case of various types of stacks and ducts associated with pollution control equipment, particularly stacks and ducts associated with baghouse-type equipment.

SUMMARY OF THE INVENTION

In accordance with the present invention, there is provided a low cost, lightweight solid state backscatter particulate monitor that overcomes the difficulties associated with current transmissometers and scattering instruments. The monitor uses optically efficient design, efficient light-to-digital signal detectors, embedded microcontrollers, an air purge system containing no moving mechanical parts and utilizes less than 2 watts. The monitor provides automatic setup, span and sample operations suitable for measurement of particulates in a gas stream.

In preferred embodiments, the monitor of the invention establishes a transmitted beam of radiant energy into a gas stream that is reflected off particulates in the stream. The monitor includes optics that concentrate the reflected energy onto a detector that generates a signal representative of the amount of energy reflected from the particulates. The radiant energy source, preferably a source of infrared energy, is turned off periodically and the detector output is monitored for ambient energy. A spanning infrared emitting diode (IRED) is provided to periodically illuminate the detector and determine proper instrument operation. An embedded microprocessor sets up the monitor automatically, processes the signal from the detector in setup mode, ambient light mode, signal mode, and span mode. The microprocessor monitors the condition of the instrument, controls the functions of the source, the spanning light emitting diode, and determines the level of the particulates.

In one embodiment, the invention is used as a monitor to determine failure of air pollution control equipment, for example, broken or leaking bags in baghouse pollution control equipment. In this embodiment, the monitor of the invention is mounted to a stack or duct and serves to compare the backscatter level to established levels when the gas stream is clean, determine acceptability to established dust level values, and communicate particulate level conditions to the facility operator. Four conditions are indicated, preferably by using two contacts on the monitor. Both contacts closed indicates that both the monitor and particulate levels are acceptable. If both contacts are open, either the monitor has failed or the power is off. If only one contact is closed, either a mid level warning is indicated or a high level warning is indicated, depending upon the contact.

In another embodiment, the monitor is used as a mass particulate monitor where the microprocessor monitors the condition of the instrument, controls the functions of the source, the spanning light emitting diode, and provides an output of monitor and particulate levels into the facility data acquisition system. Signal output options include, digital, voltage or amperage proportional to the instrument backscatter signal.

BRIEF DESCRIPTION OF THE DRAWINGS

Some of the objects having been stated, other objects will appear as the description proceeds, when taken in connection with the accompanying drawings, in which.

DETAILED DESCRIPTION OF THE INVENTION

While the present invention will be described more fully hereinafter with reference to the accompanying drawings, in which aspects of the preferred manner of practicing the present invention are shown, it is to be understood at the outset of the description which follows that persons of skill in the appropriate arts may modify the invention herein described while still achieving the favorable results of this invention. Accordingly, the description which follows is to be understood as being a broad, teaching disclosure directed to persons of skill in the appropriate arts, and not as limiting upon the present invention.

Figure 1:
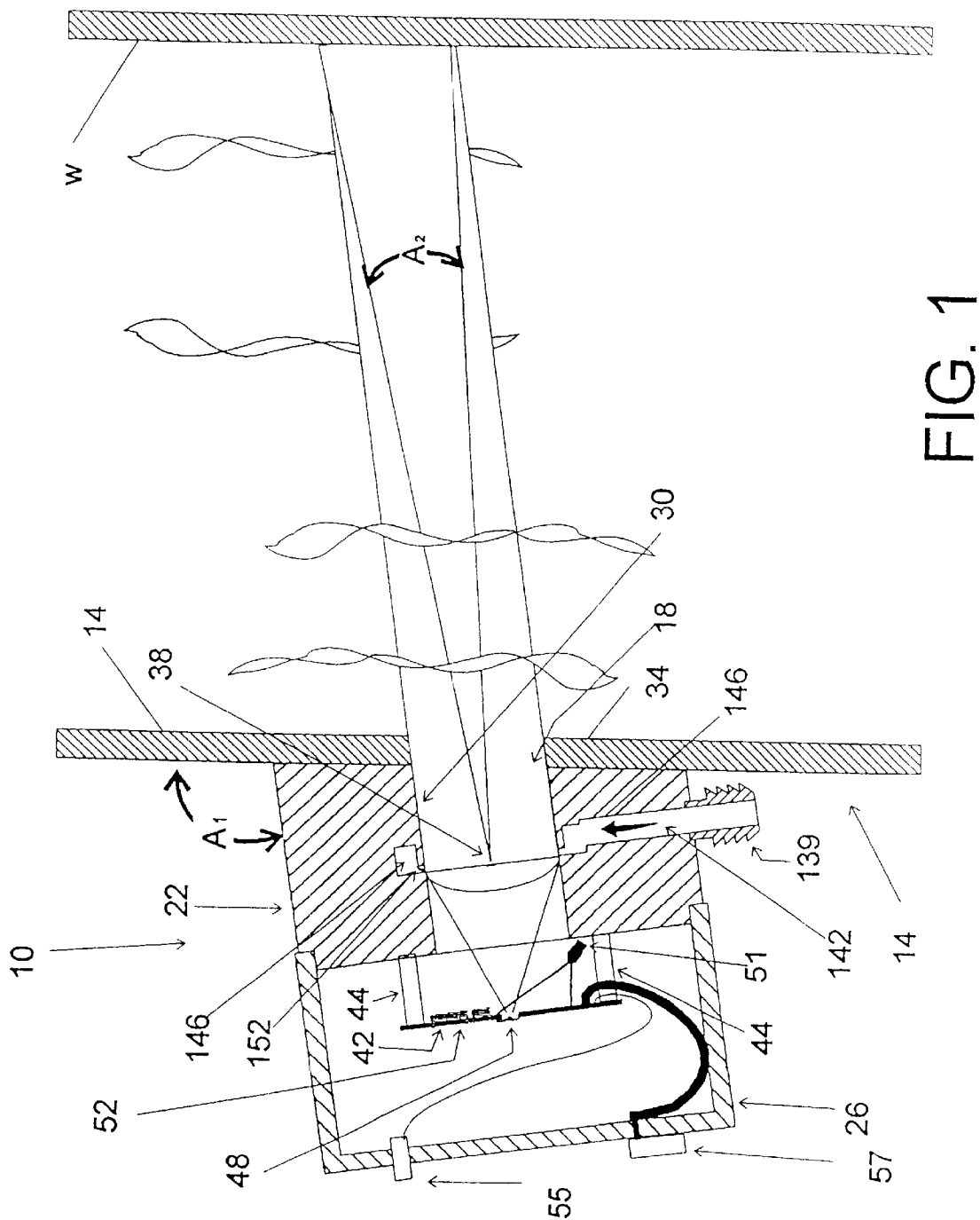
FIG. 1 is a cross-sectional view of the instrument as mounted to a duct.

Referring to the drawings, and particularly to FIG. 1, there is shown a backscatter monitor 10 constructed in accordance with present invention, installed on a smokestack 14 associated with pollution control equipment such as a baghouse (not shown). As known in the art, smokestack 14 carries a gas stream that should have a low particulate level due to dust having been removed from the stream by the baghouse. However, when a bag leaks or breaks in the baghouse, particulates in the gas stream rise to an unacceptable level and it is essential that the equipment operator be immediately notified of this condition by a signal from monitor 10.

Monitor 10 is mounted to smokestack 14 by conventional means known in the art, for example, by provision of a window 18 in the side of stack 14 and mating flange elements (not shown) that are located around window 18 and on monitor 10. Preferably, monitor 10 is mounted so that its longitudinal axis is oriented at an angle Al from the stack which is in the range from about 100 °C. to 110 °, with an angle of about 102 ° having been found desirable. As discussed in more detail below, the angular orientation of monitor 10 assists in projecting the radiant beam into the stack at a projection angle that minimizes the reflection of radiant energy from the opposite stack wall W back to the monitor. More particularly, the radiant energy beam preferably is directed into smokestack 14 at an angle greater than twice the beam spread to minimize the effects of reflection off of the opposing wall surface.

Monitor 10 includes a cylindrical main body portion 22 of plastic or metal, or other suitable material. A cap portion 26 removably secures to main body portion 22 by latching-type fasteners, a threaded connection, or other suitable connection. Main body portion 22 includes a central passage 30 opening to the interior of smokestack 14 and opening to the interior of cap 26. A lens 34 is mounted in passage 30. A source of radiant energy is provided in the form of an infrared light-emitting diode (IRED) 38 that, in the illustrated embodiment, is secured to the center of lens 34. The source may take other forms, such as fiber optics. IRED 38 directs a narrow angle conical projection of infrared energy into smokestack 14. The angle of projection $A_2$ preferably in the range from about 5 ° C. to 20 °, with an angle of about 10° to 15° having been found suitable. For use in a small stack (e.g., less than about five feet diameter) environment at an installation such as a baghouse, IRED 38 may be a 0.081 milliamp device at a wavelength in the near infrared. A suitable IRED for this purpose is model number CLE-335 IRED manufactured by Clairex of Plano, Tex. (USA).

It will be appreciated that in the illustrated embodiment, the entire monitor 10 is mounted to smokestack 14 at the mentioned angle Al in order to provide the desired input direction for the radiant beam which is centered along the longitudinal axis of monitor 10. However, monitor 10 may also be constructed such that the beam does not radiate along the longitudinal axis of the monitor, in which case the monitor would be mounted to the stack accordingly.

Monitor 10 also includes a printed circuit board 42 located within cap 26. Circuit board 42 is conventionally mounted by four posts 44 secured to main body portion 22. Circuit board 42 mounts a solid state infrared photodetector 48 located at the focal point of lens 34 and an embedded microcontroller 52, as well as other components discussed below. Photodetector 48 preferably is. a solid state silicon pin photodetector model number 235 or 245, manufactured by Texas Instruments (USA). Microcontroller 52 may take the form of a model number BS-2 microcontroller, manufactured by Parallax, Inc. (USA).

The backscatter mode of particulate detection by monitor 10 operates as follows: Radiant infrared energy emitted by IRED 38 is projected into the gas stream of smokestack 14 at an angle and with a beam spread as described above. Infrared energy that is reflected off of the opposite stack wall W predominately reflects back above window 18 due to the indicated positioning of monitor 10 at angle $A_1$. Radiant energy that reflects or backscatters off particulates within the gas stream in smokestack 14 and which enters passage 30 is collected by lens 34 and focused on photodetector 48. The amplitude of the detector response is determined by the sum of the light reflected energy from the particulate matter, .the reflected energy from the opposite stack wall, and any radiant energy reflected into the system from outside. The signal is digitized, preferably by an amplitude-to-frequency converter within photodetector 48.

Figure 2:
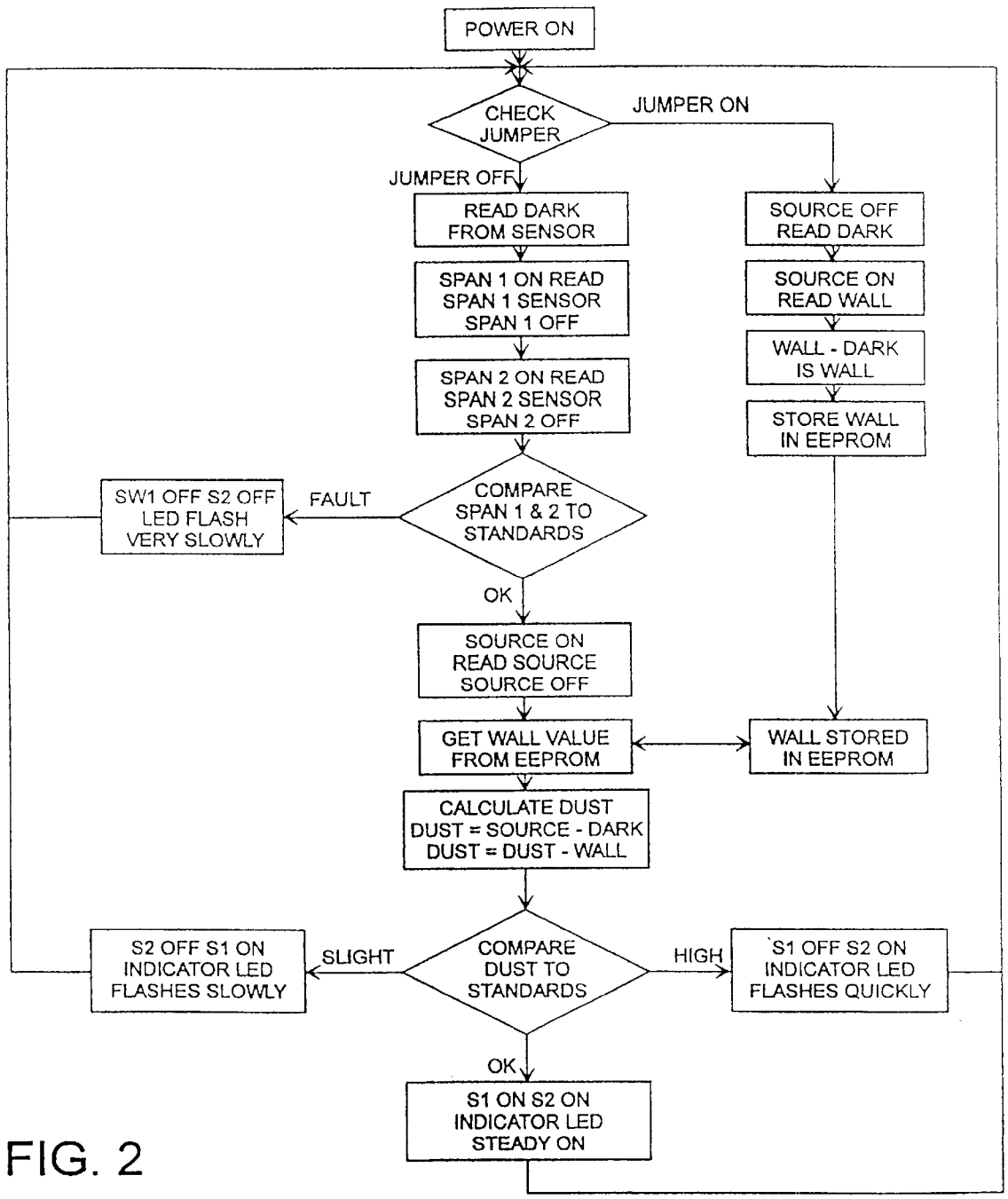
FIG. 2 is a flow chart showing the operation and logic of the monitor used as a baghouse monitor that communicates four states to the facility operator.

In one preferred usage of monitor 10 as a baghouse monitor, microprocessor 52 communicates one of four states to the facility operator according to a program stored in the microcontroller. FIG. 2 is a flow chart showing how the four states are determined and communicated to the facility operator in accordance with the level of particulates incident on the photodetector. Referring to FIG. 2, after monitor 10 is installed on stack 14, the two switch contacts (discussed below) are connected to the facility data system, and power is applied, and the microprocessor queries for the existence of an external Jumper to ground. If the jumper is in place, the instrument goes into startup mode.

In startup mode, source IRED 38 and the span IRED 51 are turned off. In this mode, photodetector 48 is only receiving the ambient infrared energy in the stack. The signal generated by the photodetector is current dependent upon infrared energy level. The current is converted to voltage by a transimpedence amplifier and to frequency within the photodetector. Thus, the frequency is dependent upon the level of infrared energy received from the duct. This value is stored in random access memory as a declared variable dark. Next the source IRED 38 is turned on by the micro processor. Because the stack is clear of dust during startup, the only infrared energy reflected back to the photodetector is from the opposing wall of the stack. The photodetector output is stored as "wall". The microprocessor subtracts the value of dark from the value of wall to determine the level of energy reflected from the opposing wall and stores this value as wall in an Eeprom. The program loops back to the beginning to check the status of the jumper. The program will stay in startup mode until the jumper is removed.

After the jumper is removed (for example, by simply cutting the jumper/lead)that may be located on the terminal strip 57, the program moves to the spancheck and sample functions.

The instrument now determines the dark level across the duct with source and span IR emitting diodes inactivated. This is stored as a variable dark in random access memory. Next span 1 switch is activated energizing the spanning diode through a resistor. The resistor value determines the current and the energy output of span 1. Typical span 1 resistor values are 1000 ohms. The -detector senses the span l value and provides a frequency signal to the microprocessor. The program then subtracts the dark from the span I signal and compares the difference to a predetermined value to validate the sensor calibration. This step is repeated for a different resistor (typically 2000 ohms) to give a lower span level. Again the difference between dark and span 2 is compared to a predetermined number to validate a mid point calibration point for the instrument.

If either of the span levels are unacceptable, output switches one and two are turned off, and the LED 55 on the face of the monitor blinks very slowly, indicating instrument fault. The program loops back to startup. As long as a span fault is present, the loop will continue.

If the span levels are acceptable the main program path (downward, FIG. 2) is followed.

If all operational conditions are acceptable, the monitor samples the dust level. The monitor again checks the current dark level by turning off all sources and spanning infrared diodes and sensing the level in the duct. The infrared source is turned on, projecting infrared energy into the duct where it is reflected off particulate and the wall. Some energy (dark) may also enter the instrument from the duct. The Eeprom wall value is retrieved. Dark and wall are subtracted from the detector output to give a dust value. The dust value is compared to predetermined standards. There are three possibilities. The first is that the dust level is high indicating an excessive level of dust. In this case one of the switches is turned off the other on and the indicator LED 55 is flashed quickly. The second is that the dust level is slight indicating an moderate level of dust. In this case the switch conditions are reversed and the indicator LED 55 is flashed slowly. If almost no dust is present, both switches are turned on and the indicator LED 55 is turned on in a steady state. In any of the three cases the instrument holds the switch conditions for a short period of time (approximately 10 seconds) and the program loops back to the beginning checking for jumper etc.

Figure 3:
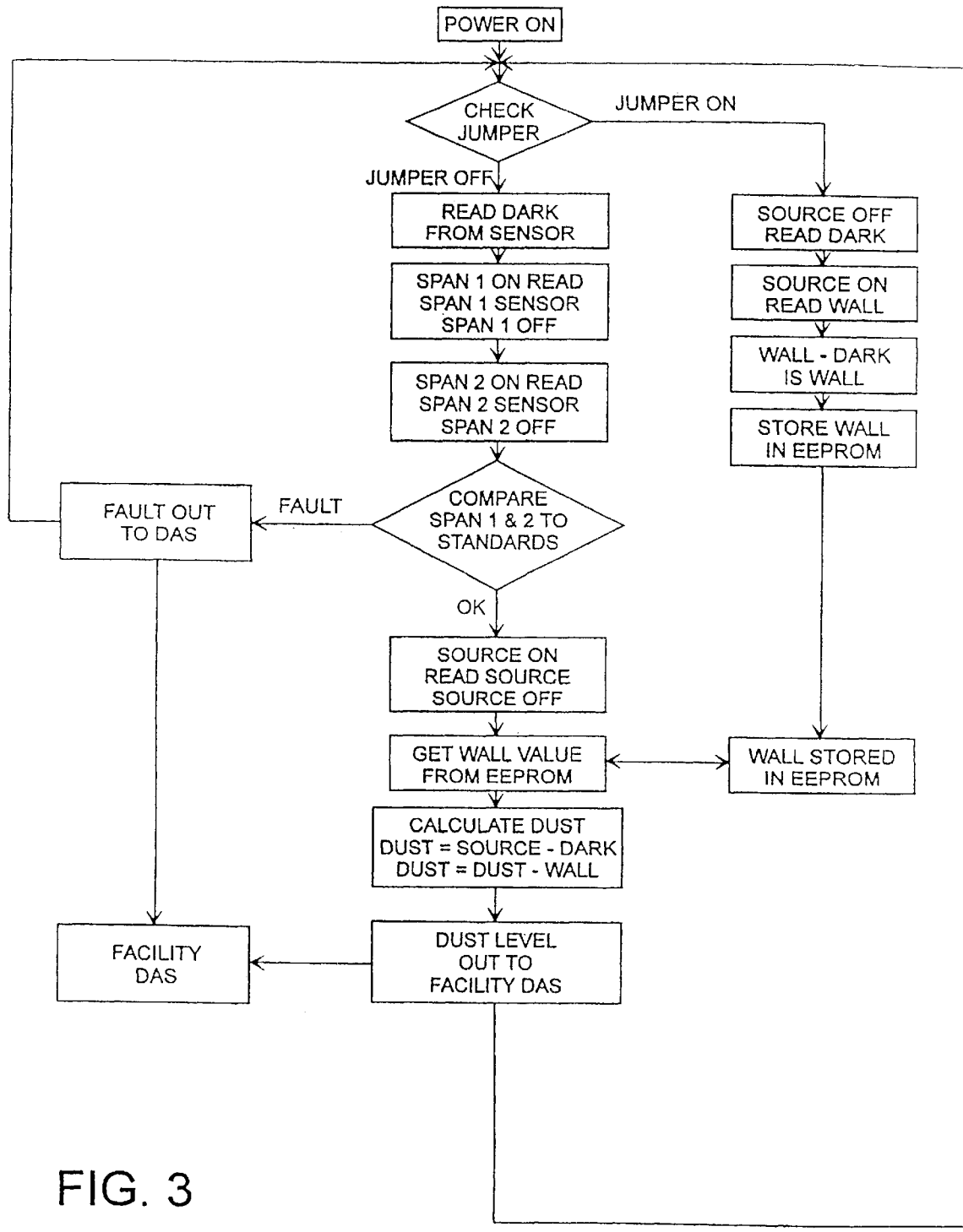
FIG. 3 is a flow chart similar to FIG. 2 for a monitor used as a particulate mass concentration monitor that communicates to the facility data acquisition system.

FIG. 3 is a flow chart similar to FIG. 2, but showing the operation and logic of the monitor when used as a particulate mass monitor. Referring to FIG. 3, after monitor 10 is installed on stack 14, the two switch contact are connected to the facility data system, and power is applied, and the microprocessor queries for the existence of an external jumper to ground. If the jumper is in place, the instrument goes into startup mode.

In startup mode source IRED 38 and the span IRED 51 are turned off. In this mode, the photodetector is only receiving the ambient infrared energy in the stack. The signal generated by the photodetector is current dependent upon infrared energy level. The current is converted to voltage by a transimpedence amplifier and to frequency within the photodetector. Thus the frequency is dependent upon the level of infrared energy received from the duct. This value is stored in ram as a declared variable "dark". Next the source IRED 38 is turned on by the micro processor. Because the stack is clear of dust during startup, the only infrared energy reflected back to the photodetector is from the opposing wall of the stack. The photodetector output is stored as "wall". The microprocessor subtracts the value of dark from the value of wall to determine the level of energy reflected from the opposing wall and stores this value in an Eeprom. The program loops back to the beginning to check the status of the jumper. The program will stay in startup mode until the jumper is removed. After the jumper is removed, the program moves to the spancheck and sample functions.

The instrument now determines the dark level across the duct with source and span diodes inactivated. This is stored as a variable dark in random access memory. Next span 1 switch is activated energizing the spanning diode through a resistor. The resistor value determines the current and the energy output of span 1. Typical span 1 resistor values are 1000 ohms. The detector senses the span 1 value and provides a frequency signal to the microprocessor. The program then subtracts the dark from the span 1 signal and compares the difference to a predetermined value to validate the sensor calibration. This step is repeated for a different resistor (typically 2000 ohms) to give a lower span level. Again the difference between dark and span 2 is compared to a predetermined number to validate a mid point calibration point for the instrument.

If either of the span levels are unacceptable, a digital span fault signal is transmitted to the data acquisition system of the facility, and the LED on the face of the instrument blinks very slowly, indicating instrument fault. The program loops back to startup. As long as a span fault is present, the loop will continue.

If the span levels are acceptable the main program path (downward, FIG. 3) is followed.

If all operational conditions acceptable, the monitor samples the dust level. The instrument again checks the current dark level by turning all sources and spanning infrared diodes and sensing the level in the duct. The infrared source is turned on, projecting infrared energy into the duct where it is reflected off particulate. and the wall. Some energy (dark) may also enter the instrument from the duct. The Eeprom wall value is retrieved. Dark and wall are subtracted from the detector output to give a dust value. The dust value is outputted to a digital to analog converter for the facility data acquisition system. Then the program loops back to the beginning checking for jumper etc.

Figure 4:
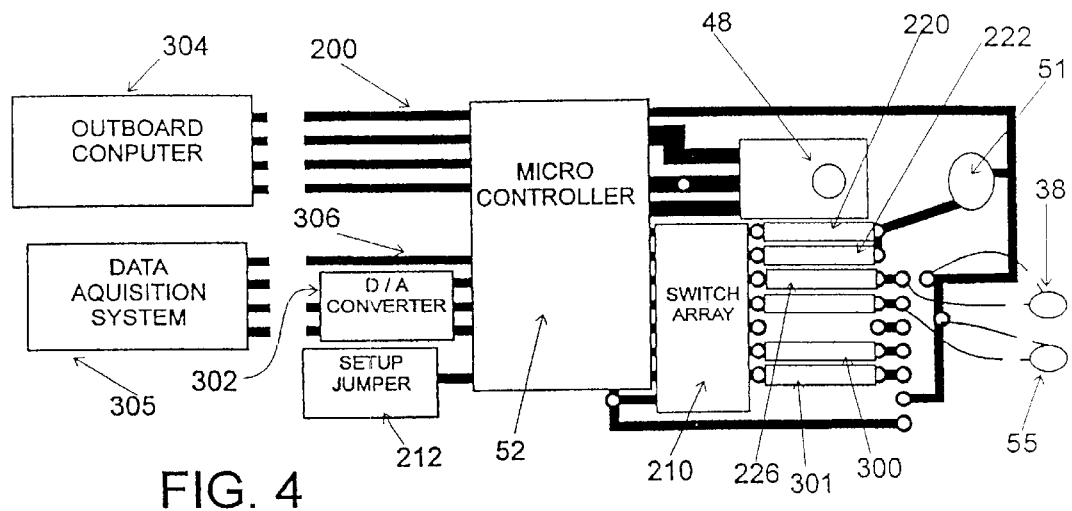
FIG. 4 is a representation of the printed circuit board that mounts the photodetector, microprocessor and related components.

FIG. 4 is an illustration of the electronic components on the circuit board. The main component is microcontroller 52 that controls all of the functions of the instrument. The microcontroller is programed using an outboard computer 304 via a four wire serial interface 200. The microprocessor controls the source IRED 38, the span IRED 51, and the indicator LED 55, via a switching array 210. A setup jumper 212 external to the instrument is connected to a port of the microcontroller. The external contacts (discussed above) preferably are located on terminal strip 57 and are connected to the switching array through resistors 300 and 301, as shown. Current control to span IRED 51 is controlled by resistors 220 and 222. Current through source IRED 38 is controlled through resistor 226. When the instrument is used in a mass monitoring mode, three pins of the microcontroller output to a 12 bit digital to analog converter 302 via a serial interface. Converter 302, in turn, communicates with the facility data acquisition system 305. One port of microcontroller 52 has a wire 306 that connects to the facility data acquisition system 305 to provide instrument status reports such as span faults. Signal output from photodetector 48 to microcontroller 52 is via a three wire interface.

Figure 5:
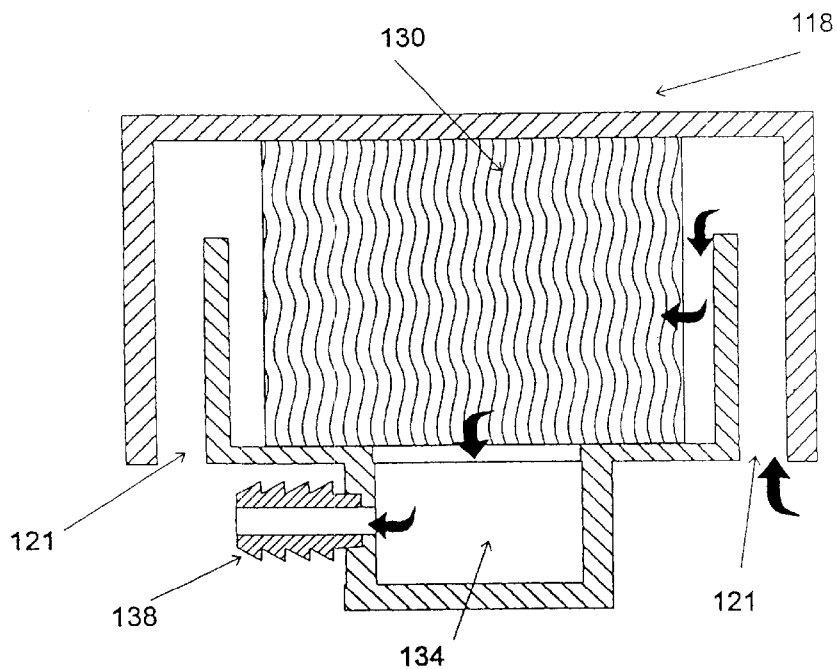
FIG. 5 is a cross-sectional view of the filter portion of the air purge system.

Referring to FIG. 5, there is shown the filter portion 118 of an air purge system 120 that provides a continuous flow of clean air across lens 34 to prevent a buildup of opaque matter on the lens surface. Filter 118 may be located in close proximity to monitor 10 external of the stack. In a preferred embodiment, air purge system 120 uses no moving parts and operates with a draft created by the pressure differential between the ambient atmosphere and the stack. In this embodiment, ambient air is drawn into the input 121 of air filter 118 which contains a conventional air filter medium 130 such as used for automobile carburetor products. Air exits medium 130 to a plenum 134 from which it flows through a conduit 138. Conduit 138 is connected to a conduit 139 on monitor 10 by a flexible hose (not shown). Conduit 138 communicates with a passage 142 in monitor main body portion 22. Passage 142 communicates with an annular cavity 146 that is also formed in main body portion 22 surrounding the front face of lens 34. Several small openings 152 (only two shown) extend from annular cavity 146 open into central passage 30 just in front of lens 34 and serve to continuously direct streams of clean air drawn through filter 118 across the front of the lens. It will be appreciated that in those cases where the pressure differential between the ambient atmosphere and the stack does not create a sufficient draft, a fan or blower may be used to provide the flow of clean air to the front face of lens 34. Alternatively, a clean compressed air source may be used. In any event, the clean air should be provided continuously in an amount sufficient to keep the particulates flowing through stack 14 from contacting lens 34 and accumulating thereon.

While the present invention has been described in connection with illustrated embodiments it will be appreciated that modifications may be made without departing from the true spirit and scope of the invention.

That which is claimed is:

1. A backscatter instrument for monitoring the level of particulates in a gas stream flowing through a stack or duct, said backscatter instrument comprising:

a radiant energy source for delivering a narrow beam of radiant energy across the stack or duct through an opening in the stack or duct wall;

a lens positioned behind the radiant energy source for receiving radiant energy backscattered from particulates in the stack or duct and focusing the radiant energy at a focal point;

the radiant energy source being positioned on the lens;

a photodetector sensitive to the band of radiant energy emitted by the radiant energy source, said photodetector being located at or near the focal point of the lens;

means responsive to the radiant energy incident on the photodetector for generating a signal representative of the intensity of incident radiant energy; and signal processing means for providing the facility operator with an indication of the particulate level in the gas stream.

2. The backscatter instrument of claim 1 wherein the signal processing means includes means for generating information concerning discrete states of particulate levels in the stack or duct.

3. The backscatter instrument of claim 2 wherein the discrete states include a low acceptable level, a high unacceptable level and at least one mid range level.

4. The backscatter instrument of claim 1 wherein the signal processing means includes means for generating information concerning the actual level of particulates in the stack or duct and communicating the information to a facility data acquisition system.

5. The backscatter instrument of claim 1 including a microcontroller providing automatic setup wherein a wall value is determined and stored.

6. The backscatter instrument of claim 1 including an air purge system for directing clean air across the face of the lens to prevent accumulation of particulates on the lens.

7. The backscatter instrument of claim 6 wherein the air purge system has no moving parts and wherein ambient air is drawn through a filter and directed to the face of the lens by a draft that utilizes the pressure differential between the ambient atmosphere and the stack or duct.

8. The backscatter instrument of claim 1 wherein the radiant energy is transmitted across the stack or duct without using a lens external to the radiant energy source, and the focusing of backscattered radiant energy at the photodetector is performed using one lens, so that the instrument has only one lens.

9. The backscatter instrument of claim 1 wherein the radiant energy source produces infrared radiant energy.

10. A method of monitoring dust levels in a stack or duct associated with a baghouse-type pollution control installation wherein the stack or duct has a diameter of less than about five feet and the fluid stream in said stack or duct, in normal operation, has an opacity less than about 5%, said method comprising the steps of:

establishing a narrow beam of radiant energy across the stack or duct;

receiving backscattered radiant energy on a single lens having a focal point, the lens being positioned behind the radiant energy source and secured thereto;

detecting the intensity of the backscattered radiant energy at or near the lens focal point;

generating a signal representative of the intensity of the radiant energy at the lens local point; and providing the system operator with an indication of the particulate level in the gas stream.

11. The backscatter instrument of claim 1 wherein the radiant energy source is secured to the lens.

12. The backscatter instrument of claim 11 wherein the radiant energy source is a light emitting diode secured to the lens.

13. The backscatter instrument of claim 11 wherein the radiant energy source is an infrared light emitting diode secured to the center of the lens.

14. The backscatter instrument of claim 1 wherein the beam of radiant energy is delivered across the stack or duct at an angle $A_1$ from the stack, angle $A_1$ being in the range from about 10020 to 110°.

15. The backscatter instrument of claim 14 wherein angle $A_1$ is greater than twice the beam spread of the beam of radiant energy.

16. The backscatter instrument of claim 1 wherein the radiant energy source, lens and photodetector are housed in a body that is secured to the exterior of the stack or duct at the location of a window in the side of the stack or duct.

17. The method of claim 10 including the step of directing clean air across the face of the lens to prevent accumulation of particulates on the lens by drawing ambient air through a filter and directing the ambient air to the face of the lens by a draft that utilizes the pressure differential between the ambient atmosphere and the stack or duct.

18. The method of claim 10 wherein the step of establishing a narrow beam of radiant energy across the stack or duct is carried out without using a lens external to the source of radiant energy, and the focusing of backscattered radiant energy is performed using one lens, so that the method is carried with only one lens.

19. The method of claim 10 wherein the step of establishing a narrow beam of radiant energy is carried out by a light emitting diode secured to the lens.

20. A backscatter instrument for monitoring the level of particulates in a gas stream flowing through a stack or duct, said backscatter instrument comprising:

a radiant energy source for delivering a narrow beam of radiant energy across the stack or duct;

a lens positioned behind the radiant energy source for receiving radiant energy backscattered from particulates in the stack or duct and focusing the radiant energy at a focal point;

the radiant energy source being positioned on the lens; and a photodetector located at or near the focal point of the lens.

* * * * *